United States Patent [19]

Vijayalakshmi et al.

[11] Patent Number: 4,833,075

[45] Date of Patent: May 23, 1989

[54] IMMOBILIZED LUCIFERASE FOR THE QUANTITATIVE DETERMINATION OF ATP

[75] Inventors: Mookambeswaran Vijayalakshmi; Rajgopal Sunanda, both of Compiegne, France

[73] Assignee: Centre National de la Recherche Scientifique, Paris, France

[21] Appl. No.: 151,663

[22] Filed: Apr. 1, 1988

Related U.S. Application Data

[63] Continuation of Ser. No. 748,804, Jun. 26, 1985, abandoned.

[30] Foreign Application Priority Data

Jun. 27, 1984 [FR] France .................................. 84 10119

[51] Int. Cl.[4] ........................ C12Q 1/66; C12N 11/00; C12N 11/02
[52] U.S. Cl. ...................................... 435/8; 435/174; 435/177; 530/354
[58] Field of Search .................... 435/8, 174, 177, 182; 530/354

[56] References Cited

U.S. PATENT DOCUMENTS 4,411,999  10/1983  Shigesada et al. ................. 435/177

4,601,981  7/1986  Vieth et al. ..................... 435/177 X

OTHER PUBLICATIONS

Romette, et al., Cinica Chimica Acta., vol. 95, 1979, pp. 249-253.

Kricka, et al., Trac, Trends in Analytical Chemistry, vol. 2, No. 11, 1983, pp. 244-247.

Ugarora, et al., Chemical Abstracts, 97:87825x, 1982, p. 366.

The Condensed Chemical Dictionary, 8th ed., VHR, N.Y., 1971, pp. 412-413.

*Primary Examiner*—David M. Naff
*Attorney, Agent, or Firm*—Armstrong, Nikaido, Marmelstein, Kubovcik & Murray

[57] ABSTRACT

Luciferase is immobilized on a membrane prepared from an absorbent albuminoid such as procine skin gelatin. The membrane may be formed by spreading a solution of porcine skin gelatin on a support and after incubation and drying removing the resultant membrane from the support. Preferably, the membrane is cross-linked with a solution of glutaraldehyde, and luciferase is immobilized by saturating the membrane with luciferase in the presence of dithiothreitol. The immobilized luciferase is particularly suitable for the quantitative determination of adenosine triphosphoric acid (ATP).

10 Claims, No Drawings

IMMOBILIZED LUCIFERASE FOR THE QUANTITATIVE DETERMINATION OF ATP

This application is a continuation of application Ser. No. 748,804 filed June 26, 1985, now abandoned.

The present invention relates to a luciferase carrier membrane for, in particular, the quantitative determination of adenosine triphosphoric acid, or ATP, as well as to a process for its production.

Luciferase is an enzyme generally extracted from luciola (glow-worm—*Photinus pyralis*). Luciferase has recently been the subject of renewed interest on account of its specificity for ATP, since it enables this acid or salts thereof to be quantitatively determined in various food products. For example, by measuring the ATP present in milk, microbial determination or determination of creatinine in diasic analysis may be performed. Quantitative determination of ATP is carried out photometrically since its reaction with the enzyme produces an emission of photons according to the following two reaction equations:

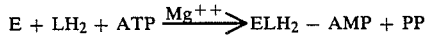

$$E + LH_2 + ATP \xrightarrow{Mg^{++}} ELH_2 - AMP + PP$$

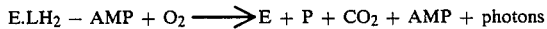

$$E.LH_2 - AMP + O_2 \longrightarrow E + P + CO_2 + AMP + photons$$

in which E denotes luciferase, E.LH$_2$-AMP the luciferine adenylate complex, P the product of the oxidation reaction producing oxyluciferine, and PP denotes pyrophosphate.

The intensity of the bioluminescence measured is directly proportional to the amount of ATP present in the product under investigation.

However, the implementation of this method has been held back for a long time by the lack of stability of luciferase. A certain number of methods for determining this enzyme have therefore been investigated. Thus, the enzyme has been "trapped" in an albumin gel to which glutaraldehyde has been added, or in a polyacrylamide gel, has been adsorbed on this latter gel or immobilised on various polysaccharide supports such as AH-Sepharose 4B or CH-Sepharose 4B using a carbodiimide or CH-Sepharose 4B using Woodward's reagent, or has even been immobilised on polysaccharide supports activated by a cyanide bromide (CNBr).

Only this latter method was regarded as satisfactory since it enables 20% of the luciferase activity to be preserved, which is a substantially higher percentage than is obtained by the other methods. On account of this, the thus immobilised luciferase is produced at a relatively high cost, that may be regarded as prohibitive for industrial applications. Furthermore, the enzyme does not have a really satisfactory stability.

One of the aims of the present invention is therefore to provide immobilised luciferase cheaply so as to enable it to be widely used industrially.

Another object of the invention is to provide a luciferase that is heat stable and stable to long-term storage.

A supplementary object of the invention is to provide a process for preparing an immobilised luciferase that is simple and may be implemented on an industrial scale.

These objectives, as well as others that will appear hereinafter, are achieved by luciferase immobilised on a membrane which, according to the present invention, is a membrane consisting of an absorbent (hydrophilic) albuminoid.

This membrane advantageously consists of porcine skin gelatin.

The present invention also relates to a process for producing such a luciferase carrier membrane, according to which an absorbent albuminoid is dissolved in a slightly acid buffer so as to obtain a homogeneous membrane, this homogeneous membrane is cross-linked by means of a glutaraldehyde solution at a slightly acid pH, and the membrane thus obtained is saturated with a specific amount of luciferase.

The slightly acid buffer preferably consists of a solution of sodium phosphate of pH 6.8.

The solution obtained by dissolving the absorbent albuminoid in the buffer advantageously contains 6% by weight of this albuminoid.

A homogeneous membrane is preferably prepared from this solution by spreading it, after a short incubation at a temperature between 25° C. and 50° C., over a suitable support from which it will be removed after drying.

Incubation is advantageously carried out for one hour at a temperature of 37° C.

The suitable support preferably consists of a polycarbonate film.

The homogeneous membrane is advantageously cross-linked by a 0.5% by volume solution of glutaraldehyde.

The pH of the glutaraldehyde solution is preferably the same as that of the phosphoric acid buffer.

The luciferase of the membrane is advantageously saturated in the presence of dithiothreitol (DTT).

The following description, which is by way of example and is not intended to be limiting, will enable those skilled in the art to understand better the present invention as well as the advantages of the latter.

Luciferase is prepared according to a known method from dried glow-worm (for example *Photinus pyralis*) abdomens in a 0.1M arsenate buffer of pH 7.4, as described by S. RAJGOPAL et al in J. of Chromatography 1982, No. 243, pages 164–167. The extract thus obtained is dialysed for 24 hours in 0.02M (pH=7.8) tris-acetate in the presence of 1 mM of ethylenediaminotetraacetic acid (EDTA) and with three changes of buffer.

Of the available absorbent albuminoid products, the Applicants have chosen to use porcine skin gelatin for making a membrane on which the luciferase will be immobilised.

The porcine skin gelatin is first of all dissolved in a 0.02M (pH=6.8) sodium phosphate buffer so as to obtain a solution in which the gelatin concentration is 6% by weight. This solution is then incubated for one hour at 37° C. The solution obtained is next spread over a polycarbonate film, which is a suitable material on account of its non-adhesion: for example, 15 ml of this solution is spread over a 15 cm$^2$ surface area of such a film. The film is then allowed to dry for about 10 hours. A homogeneous membrane is thereby formed on this polycarbonate film, from which it can easily be detached.

This homogeneous membrane is cross-linked by soaking strips or squares of the latter for a short time, of the order of 5 minutes, in a buffer identical to the above buffer but also containing 0.5% by volume of glutaraldehyde. The cross-linked membrane is then washed several times with the same buffer so as to remove excess glutaraldehyde.

The luciferase is immobilised on the cross-linked membrane by saturation with a specific amount of luciferase, preferably in the presence of dithiothreitol (DTT). After one hour at ambient temperature, the cross-linked membrane on which the luciferase is immobilised is washed with the buffer already described above.

The following tests enabled the various parameters of the process to be determined so as to obtain luciferase immobilised on a protein membrane.

(1) Effect of glutaraldehyde

Various homogeneous membranes were cross-linked with 0.02M (pH 6.8) sodium phosphate buffers containing glutaraldehyde at concentrations varying from 0.5 to 5.0%. The cross-linked membranes thus obtained—in fact discs of the latter—were immersed in a solution of luciferase in the presence of DTT for one hour at a temperature of +4° C. 500 μl of enzyme was immobilised on each 1 cm$^2$ in the presence of 100 μl of DTT (9.5 mg of DTT in 10 ml of morpholinopropane sulphonate (MOPS)).

It was therefore shown that the maximum activity of luciferase is obtained with a glutaraldehyde concentration of 0.5%. This activity decreases when the glutaraldehyde concentration increases to 1%, and then becomes greater than 2%. The enzyme activity of luciferase increases linearly between a concentration of 1% and 2%.

It should be remembered that luciferase in solution is completely inactivated by glutaraldehyde in one hour, and that dithiothreitol has no effect on this inactivation rate.

(2) Effect of contact time of luciferase with cross-linked membranes

Discs of membranes cross-linked in the presence of 0.5% glutaraldehyde are left in contact with luciferase for various durations. The maximum contact time is one hour. Significant losses in activity were established for various durations.

In the case of luciferase in solution, it is found that after one hour this solution has a residual enzyme activity of 10% with respect to that of the freshly prepared solution. If this solution contains DTT, this residual activity is 50%.

(3) Effect of pH during cross-linking

Discs of homogenous membrane were placed in a 5% glutaraldehyde solution in a 0.02M sodium phosphate buffer for one hour at +4° C.

It was found that the enzyme activity of luciferase subsequently immobilised on such membranes is a maximum when the pH of the buffer is 6.8.

Of course, it is known that cross-linking in the presence of glutaraldehyde is promoted by an acid pH, and in particular is a maximum at pH 5. In contrast, the maximum activity of luciferase in solution is at pH 7.8. Experimentation has shown that it is practically impossible to determine quantitativey the activity of luciferase immobilised on a membrane cross-linked at pH 5.

(4) Effect of temperature during immobilisation

The optimum immobilisation temperature corresponds to the maximum enzyme activity, and was determined by varying the temperature during contact with discs of cross-linked membranes. This temperature is 18°–20° C., i.e. ambient temperature.

The characteristics of luciferase immobilised according to the process of the present invention were revealed by the following experiments.

(1) Immobilisation efficiency

About 30 to 40% of the activity of the luciferase in contact with a cross-linked membrane as described above is retained. A specific activity of 100 to 200 units per mg of membrane was measured. In addition, the same membrane may be used several times.

After use, the membrane discs may be washed and kept in a 0.02M sodium phosphate buffer (pH 6.8) in the presence of dithiothreitol in order to preserve their activity.

The enzyme immobilised on such discs and preserved under these conditions is stable for at least 16 days.

The fact that the membrane prepared according to the present invention can be used over such a long period of time constitutes an important advantage as regards industrial use.

(2) Stability over time

The optimum conditions for each parameter studied were deduced from the previous experiment.

Luciferase in contact with a membrane that was cross-linked in the presence of 0.5% glutaraldehyde at pH 6.8 for one hour at ambient temperature in the presence of DTT has a stable enzyme activity: two hours after the end of contact the enzyme activity is 95% and remains at this value.

In the case of luciferase in solution, the activity level is only 54%.

(3) Temperature stability

On heating cross-linked membrane discs containing luciferase, a stability in enzyme activity up to about 20°–25° C. is found, followed by a relatively slow decrease in activity. The mechanical strength of the discs is not at all affected by the temperature.

When luciferase is in solution, its maximum enzyme activity is at 4° C. and then decreases very rapidly and becomes zero before 40° C.

To be able to obtain a membrane that can be used at ambient temperature constitutes a great advantage insofar as no particular precautions in use are necessary. An ATP detector employing such a membrane may be included without basically having to alter a chain of control in industry. Furthermore, the activity of living organisms can be measured.

(4) pH stability

The optimum pH for both the immobilised enzyme and the enzyme in solution is 7.4.

(5) Concentration of luciferase and ATP

It may be noted with regard to these two products that the support (porcine skin gelatin) has no affect on the affinity of the substrate (luciferine or ATP) for luciferase. There are therefore no problems of diffusion of immobilised enzyme to the surface of the membrane and its products.

Immobilisation of luciferase on an absorbent albuminoid membrane such as porcine skin gelatin thus enables a membrane to be obtained that is easy to use, has an acceptable life, and has a high specificity for ATP. In actual fact, a linear response of the luminous intensity peak was observed with ATP concentrations ranging from $10^2$ to $10^6$ picograms of ATP per milliliter of solution.

What is claimed is:

1. A process for producing a membrane having luciferase immobilized thereon, comprising the steps of, dissolving a porcine skin gelatin in a slightly acidic buffer and obtaining a homogenous membrane, cross-linking said homogenous membrane in a glutaraldehyde solution at a slightly acidic pH, and saturating the cross-linked membrane with luciferase in the presence of dithiothreitol to obtain a membrane which is saturated with luciferase.

2. A process according to claim 1, wherein the slightly acid buffer is a solution of sodium phosphate having a pH of 6.8.

3. A process according to claim 1, wherein 6% by weight of porcine skin gelatin is dissolved in said buffer.

4. A process according to claim 1, wherein after dissolving said porcine skin gelatin, the resultant solution is incubated at between 25° and 50° C. for a short time, spread on a suitable support, dried to form a membrane, and the membrane is removed from the support.

5. A process according to claim 4, wherein incubation is carried out for one hour at 37° C.

6. A process according to claim 4, wherein the suitable support consists of a polycarbonate film.

7. A process according to claim 1, wherein the glutaraldehyde solution contains 0.5% by volume glutaraldehyde.

8. A process according to claim 7, wherein the pH of the said glutaraldehyde solution is the same as that of the said buffer.

9. A membrane on which luciferase is immobilized prepared according to the process of claim 1.

10. A process for quantitatively determining the presence of adenosine triphosphoric acid comprising the step of applying a material to be tested to a membrane on which luciferase is immobilized and measuring intensity of bioluminescence produced, said membrane containing immobilized luciferase being prepared by the steps of, dissolving a porcine skin gelatin in a slightly acidic buffer and obtaining a homogenous membrane, cross-linking said homogenous membrane in a glutaraldehyde solution at a slightly acidic pH, and saturating the cross-linked membrane with luciferase in the presence of dithiothreitol to obtain a membrane which is saturated with luciferase.

* * * * *